(12) United States Patent
Wu et al.

(10) Patent No.: US 11,326,449 B2
(45) Date of Patent: May 10, 2022

(54) METHOD FOR DETERMINING THREE-DIMENSIONAL IN-SITU STRESS BASED ON DISPLACEMENT MEASUREMENT OF BOREHOLE WALL

(71) Applicant: INSTITUTE OF ROCK AND SOIL MECHANICS, CHINESE ACADEMY OF SCIENCES, Wuhan (CN)

(72) Inventors: Zhenjun Wu, Wuhan (CN); Hua Tang, Wuhan (CN); Yuqiao Qin, Wuhan (CN)

(73) Assignee: INSTITUTE OF ROCK AND SOIL MECHANICS, CHINESE ACADEMY OF SCIENCES, Wuhan (CN)

(*) Notice: Subject to any disclaimer, the term of this patent is extended or adjusted under 35 U.S.C. 154(b) by 204 days.

(21) Appl. No.: 16/802,034

(22) Filed: Feb. 26, 2020

(65) Prior Publication Data

US 2021/0156249 A1    May 27, 2021

(30) Foreign Application Priority Data

Nov. 27, 2019 (CN) .......................... 201911183046.0

(51) Int. Cl.
*E21B 49/06* (2006.01)
*E21B 49/00* (2006.01)
*G01N 33/24* (2006.01)

(52) U.S. Cl.
CPC ............ *E21B 49/06* (2013.01); *E21B 49/006* (2013.01); *G01N 33/24* (2013.01)

(58) Field of Classification Search
CPC ......... E21B 49/006; E21B 49/06; E21B 25/10
See application file for complete search history.

(56) References Cited

U.S. PATENT DOCUMENTS

| | | | | |
|---|---|---|---|---|
| 3,969,929 A | * | 7/1976 | Shaw | E21B 49/006 73/783 |
| 3,992,095 A | * | 11/1976 | Jacoby | E21B 47/002 356/32 |
| 4,813,278 A | * | 3/1989 | Kosugi | E21B 49/006 73/152.11 |
| 9,359,891 B2 | * | 6/2016 | Galvan-Sanchez | E21B 49/00 |
| 10,370,965 B2 | * | 8/2019 | Hegeman | G01V 11/00 |
| 10,539,014 B2 | * | 1/2020 | Han | G01V 1/34 |

(Continued)

*Primary Examiner* — Shane Bomar
(74) *Attorney, Agent, or Firm* — Hemisphere Law, PLLC; Zhigang Ma

(57) ABSTRACT

Disclosed is a method for determining three-dimensional in-situ stress based on displacement measurement of borehole wall, including the following steps: selecting a testing borehole section for in-situ stress testing; arranging 6-9 measurement points in the testing borehole section; using a coring drill to perform a radial cut around the displacement measurement device to relieve the stress at the measurement point; cutting off the drilled core by the coring drill; recovering the sidewall coring device and removing the cores, and then measuring the elastic deformation parameters of each core; The beneficial effect of the technical scheme proposed in this disclosure is: the method provided by this disclosure overcomes the disadvantage that the measurement can only be performed at the bottom of a borehole and thus it has a wider application range.

1 Claim, 4 Drawing Sheets

(56) References Cited

U.S. PATENT DOCUMENTS

| | | | | |
|---|---|---|---|---|
| 10,655,414 | B1* | 5/2020 | Wang | E21B 49/006 |
| 11,168,562 | B2* | 11/2021 | Eng | G01V 1/50 |
| 2009/0133486 | A1* | 5/2009 | Tchakarov | E21B 49/006 |
| | | | | 73/152.02 |
| 2009/0164128 | A1* | 6/2009 | Tchakarov | E21B 49/10 |
| | | | | 702/11 |
| 2017/0204726 | A1* | 7/2017 | Lecampion | H04B 10/677 |
| 2019/0330981 | A1* | 10/2019 | Lei | E21B 49/006 |

* cited by examiner

METHOD FOR DETERMINING THREE-DIMENSIONAL IN-SITU STRESS BASED ON DISPLACEMENT MEASUREMENT OF BOREHOLE WALL

FIELD OF THE DISCLOSURE

The disclosure relates to method for determining three-dimensional in-situ stress based on displacement measurement of borehole wall.

BACKGROUND

The crustal stress state is one of the essential basic data when dealing with deep rock mass problems in civil engineering, mining energy engineering and other fields. In civil engineering, the high in-situ stress state of deep rock mass may induce rock mass failure, collapse or burst after engineering disturbance. In nuclear waste treatment engineering, rock mass with high in-situ stress and good integrity are denser and have lower permeability, which helps to prevent the migration of pollutants. In the exploration and exploitation of unconventional oil and gas resources, the in-situ stress of the original rock directly determines the stability of the borehole wall, the direction of the horizontal well and the development of the fractures, which are important parameters to improve the exploitation efficiency.

The source of crustal stress is very complicated, in addition to the gravity of the overlying rock and soil, the tectonic stress caused by the crustal tectonic movement will also have a great impact on the stress state of the rock and soil. Therefore, in-situ test is essential to accurately obtain the ground stress field. At present, the in-situ stress testing methods that are commonly used include stress relief method, hydraulic fracturing method, borehole breakout method, etc. Among them, the application of stress relief method is the most common, and the relevant testing technology is relatively mature and perfect. However, the stress relief method has some limitations in practical use, especially in deep boreholes that are affected by complex test conditions, and it is difficult to obtain ideal results in many cases.

A literature search of the existing three-dimensional in-situ stress measurement methods and testing techniques found that most of the current stress relief testing procedures can be summarized as follows: first, drilling a pilot hole with small diameter on the complete rock, which will relieve the elastic stress of the rock around the pilot hole. After the drilling was stopped, the rock pressure around the pilot hole reached equilibrium again. The next step is to put a stress measuring instrument into the pilot hole and glue the strain gauge to the wall of the pilot hole. Then releasing the stress in the surrounding rock around the stress measuring instrument, while the strain gauge records the strain generated during this process. If the elastic modulus and Poisson's ratio of the rock are known, and at least six different values of normal strain can be obtained in different directions, then based on the mathematical relationship between the strain and the far-field stress component of the surrounding rock, and through using the least square method, the six components of the far-field stress can be obtained, and the three-dimensional ground stress state of the measurement point can be determined. However, in the deep and complicated drilling conditions, especially in shale gas exploration wells or development wells, the stress relief method measurement still has the following disadvantages:

(1) The traditional stress relief method requires measurement at the bottom of the borehole, and after reaching a predetermined depth, the drill bit needs to be replaced with a special equipment to clean the bottom of the borehole and drill the pilot hole. As the depth of shale gas wells generally exceed 2000 m, lifting and replacement of drill bits are cumbersome and do not have the conditions for practical operation;

(2) Because thick mud is needed to maintain the stability of borehole wall of deep drilling, the actual test environment in the borehole is a high-temperature and high-pressure environment. Hence thick mud and rock debris often exist in the borehole wall. However, in the strain relief method, strain rosette is used, but it is very difficult to stick the strain rosette. In addition, electronic components often fail in this environment and therefore the ground stress parameters cannot be obtained correctly;

(3) The traditional stress relief method needs to obtain the elastic modulus and Poisson's ratio of the rock mass through supplementary laboratory tests. However, due to the particularity of deep drilling construction, it is generally difficult to obtain the core at the measurement point, and the elastic parameters of the rock mass obtained by other indirect methods are often inaccurate.

SUMMARY

A technical problem to be solved by the disclosure is to overcome the above shortcomings of the method for determining the three-dimensional in-situ stress of rock mass based on the borehole bottom strain measurement, and to provide a method for determining the three-dimensional in-situ stress of rock mass based on high-precision measurement of the displacement of deep borehole wall. This method is based on the theory of linear elastic rock mechanics, that is, there is a certain mathematical relationship between the borehole wall displacement and the three-dimensional ground stress tensor in the far field. This method is feasible and easy to operate. As long as at least six displacement components in different directions on a small section of borehole wall can be obtained, the relation between displacement of borehole wall and stress in the far field can be established, and the six in-situ stress components at the measurement point can be obtained.

A method for determining three-dimensional in-situ stress based on displacement measurement of borehole wall, including the following steps:

S1: conducting well logging analysis in a shale gas exploration borehole or shale gas drilling borehole, and based on the results of the logging analysis, selecting a testing borehole section for in-situ stress testing, and then lowering the sidewall coring device to a depth of 2000-3000 meters, wherein the diameter of the shale gas exploration borehole is between φ139.7 and φ339.725 mm;

S2: arranging 6-9 measurement points in the testing borehole section, and the measurement points are arranged in the form of a plum blossom, wherein the angles between the drilling axis of different measurement points is 55°-65°, and the distance in the axial direction is 90-120 mm;

S3: placing a displacement measurement equipment near a measurement point at a distance of 10-15 mm in the radial direction and piercing the mud layer of the borehole wall and against the borehole wall, after the displacement measurement device contacts the measurement point, using a coring drill to perform a radial cut around the displacement measurement device to relieve the stress at the measurement point, during the stress relief process, the displacement measurement device continuously records the radial displacement change of the borehole wall during the stress relief process and transmits it to the ground in real time through a cable, after the displacement change is stable, the stress relief process is completed and the radial displacement value in one direction is obtained, wherein the size of the coring drill is between φ25-40 mm, and the stress relief depth is 40-65 mm;

S4: after the strain relief process is completed, cutting off the drilled core by the coring drill, then rotating the sidewall coring device and repeating the stress relief and sidewall coring operations at other measurement points to obtain radial displacement values in 6-9 different directions;

S5: after the measurement of all measurement points is completed, recovering the sidewall coring device and removing the cores, and then measuring the elastic deformation parameters of each core, including the elastic modulus and Poisson's ratio through indoor supplementary tests, then combined with 6-9 radial displacement values in different directions obtained by high-precision displacement measurement, a set of linear equations including elastic deformation parameters, radial displacements and far-field stress are obtained, and the three-dimensional ground stress state of the measurement points is obtained.

The beneficial effect of the technical scheme proposed in this disclosure is: compared with the existing method of determining the three-dimensional in-situ stress of the measurement point by measuring the strain at the bottom of the borehole, the method provided by this disclosure overcomes the disadvantage that the measurement can only be performed at the bottom of a borehole, and at the same time it uses a high-precision displacement measurement device that is waterproof and pressure-resistant to replace the strain measurement device adopted in traditional method, thus overcoming the disadvantages that strain gauges cannot be stuck and used under complex mud conditions, so the method provided in this disclosure can be applied to shale gas exploration wells and development wells with a depth of more than 2000-3000 m. According to the results of indoor tests, the displacement test accuracy of method provided by this disclosure reaches 0.1 micron, and at the same time, the instrument can test at an external pressure of 60 MPa and a temperature of 80° C. Compared with other in-situ stress testing methods that can only be tested under ordinary conditions, the in-situ stress testing method provided by this disclosure has a wider application range.

Compared with prior art, the method provided by this disclosure has the following advantages and effects:

(1) Compared with most existing stress relief methods that can only perform the measurement at the bottom of a borehole, this method can directly perform in-situ stress measurement at any depth in the borehole;

(2) Compared with the existing strain rosette measurement method in the current stress relief method, this method uses a waterproof and pressure-resistant high-precision displacement measuring device to directly pierce the mud protection layer on the borehole wall and thus can be directly applied to the deep borehole environment filled with mud;

(3) After the stress relief measurement is completed, the cores at the measurement points can be collected. Therefore, after the measurement is completed, the lithological mechanical parameters of these cores can be obtained through indoor supplementary tests for determining the three-dimensional ground stress field;

(4) Compared with the existing stress relief method, the diameter of the drilling borehole for stress relief is small and the drilling depth is shallow, which can effectively improve the success rate of the measurement, and the measurement time of a single measurement point can be shortened to 15-20 minutes.

BRIEF DESCRIPTION OF THE DRAWINGS

Accompanying drawings are for providing further understanding of embodiments of the disclosure. The drawings form a part of the disclosure and are for illustrating the principle of the embodiments of the disclosure along with the literal description. Apparently, the drawings in the description below are merely some embodiments of the disclosure, a person skilled in the art can obtain other drawings according to these drawings without creative efforts. In the figures.

DETAILED DESCRIPTION OF PREFERRED EMBODIMENTS

Two embodiments are provided below to further explain the method provided by the present invention.

Embodiment 1

Figure 1:
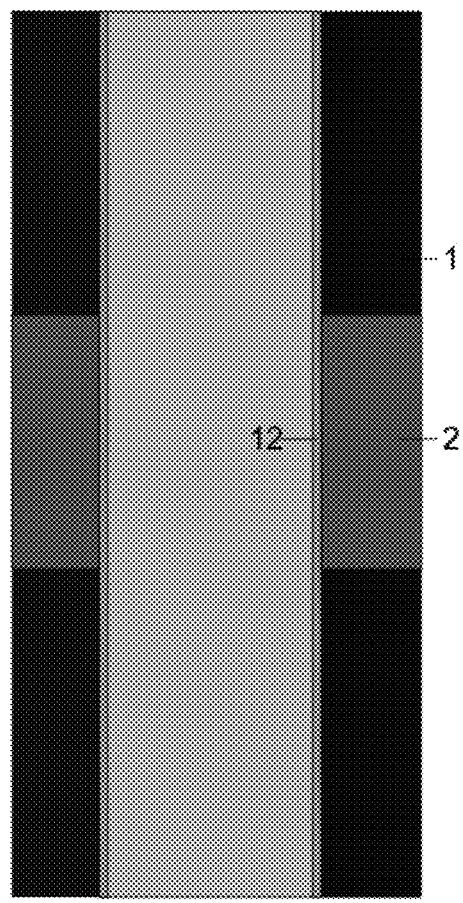
FIG. 1 is a schematic diagram of shale gas exploration borehole provided by this disclosure.
Figure 2:
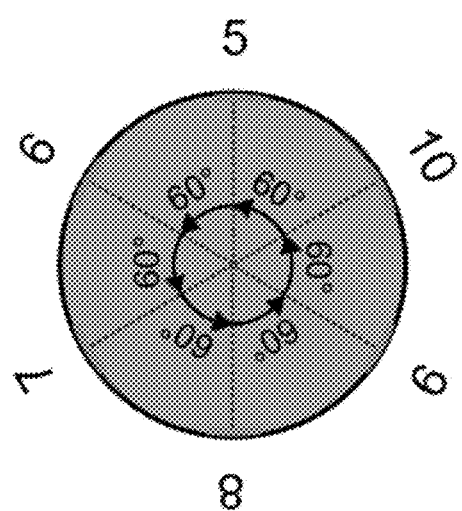
FIG. 2 is a measurement points layout section provided by this disclosure.
Figure 3:
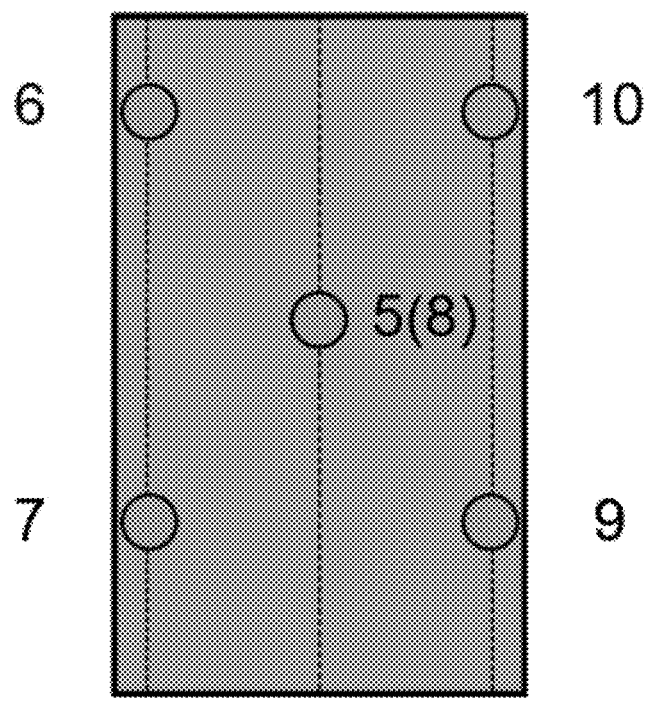
FIG. 3 is a measurement points layout sideview provided by this disclosure.
Figure 4:
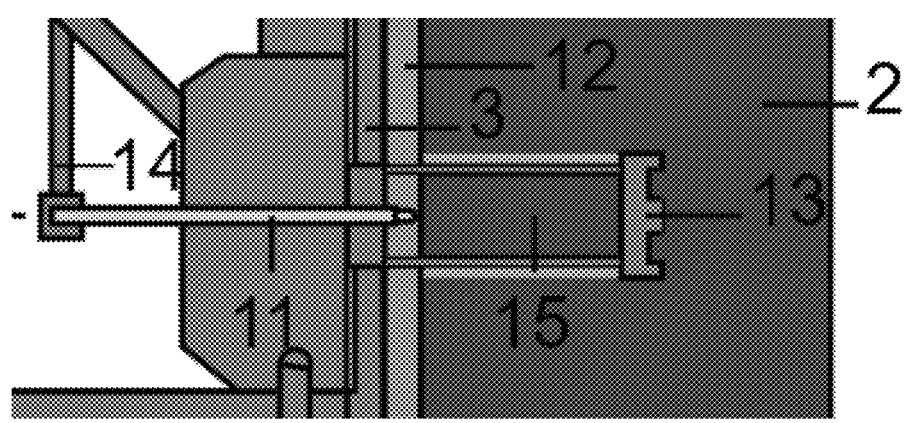
FIG. 4 is a schematic diagram of borehole wall stress relief operation provided by this disclosure.

A method for determining three-dimensional in-situ stress based on displacement measurement of borehole wall, including the following steps:

S1: conducting well logging analysis in a shale gas exploration borehole 1 or shale gas drilling borehole, and based on the results of the logging analysis, selecting a testing borehole section for in-situ stress testing, and then lowering the sidewall coring device to a depth of 2000-3000 meters, wherein the diameter of the shale gas exploration borehole 1 is between φ139.7 and φ339.725 mm, in this embodiment, the diameter of the shale gas exploration borehole 1 is about φ158.75 mm, the sidewall coring device is lowered to a depth of 2100 or 2300 or 2600 or 2800 or 3000 meters;

S2: arranging 6-9 measurement points in the testing borehole section 2, and the measurement points are arranged in the form of a plum blossom, wherein the angles between the drilling axis of different measurement points is 55°-65°, and the distance in the axial direction is 90-120 mm, as illustrated in FIG. 2 and FIG. 3, in this embodiment, arranging 6 measurement points, namely the first measurement point 5, the second measurement point 6, the third measurement point 7, the fourth measurement point 8, the fifth measurement point 9, and the sixth measurement point 10, the angles between the drilling axis of different measurement points is 55° or 58° or 61° or 63° or 60°, and the distance in the axial direction is 90 mm;

S3: as illustrated in FIG. 4, placing a displacement measurement equipment near the first measurement point 5 at a distance of 10-15 mm in the radial direction and piercing the mud layer 12 of the borehole wall and against the borehole wall, after the displacement measurement device 11 contacts the first measurement point 5, using a coring drill 13 to perform a radial cut around the displacement measurement device 9 to relieve the stress at the first measurement point 5, during the stress relief process, the displacement measurement device 11 continuously records the radial displacement change of the borehole wall during the stress relief process and transmits it to the ground in real time through a cable 14, after the displacement change is stable, the stress relief process is completed and the radial displacement value in one direction is obtained, wherein the size of the coring drill is between φ25-40 mm, and the stress relief depth is 40-65 mm, in this embodiment, the size of the coring drill is φ25.4 mm, and the stress relief depth is 44.5 mm;

S4: after the strain relief process is completed, cutting off the drilled core 15 by the coring drill 13, then rotating the sidewall coring device 3 and repeating the stress relief and sidewall coring operations at other measurement points to obtain radial displacement values in 6 different directions;

S5: after the measurement of all measurement points is completed, recovering the sidewall coring device 3 and removing the cores 15, and then measuring the elastic deformation parameters of each core, including the elastic modulus and Poisson's ratio through indoor supplementary tests, then combined with 6-9 radial displacement values in different directions obtained by high-precision displacement measurement, a set of linear equations including elastic deformation parameters, radial displacements and far-field stress are obtained, and the three-dimensional ground stress state of the measurement points is obtained.

Embodiment 2

A method for determining three-dimensional in-situ stress based on displacement measurement of borehole wall, including the following steps:

S1: conducting well logging analysis in a shale gas exploration borehole 1 or shale gas drilling borehole, and based on the results of the logging analysis, selecting a testing borehole section for in-situ stress testing, and then lowering the sidewall coring device to a depth of 2000-3000 meters, wherein the diameter of the shale gas exploration borehole 1 is between φ139.7 and φ339.725 mm, in this embodiment, the diameter of the shale gas exploration borehole 1 is about φ174.6 mm, the sidewall coring device is lowered to a depth of 2900 meters;

S2: arranging 6-9 measurement points in the testing borehole section 2, and the measurement points are arranged in the form of a plum blossom, wherein the angles between the drilling axis of different measurement points is 55°-65°, and the distance in the axial direction is 90-120 mm, as illustrated in FIG. 2 and FIG. 3, in this embodiment, arranging 6 measurement points, namely the first measurement point 5, the second measurement point 6, the third measurement point 7, the fourth measurement point 8, the fifth measurement point 9, and the sixth measurement point 10, the angles between the drilling axis of different measurement points is 55°, and the distance in the axial direction is 120 mm;

S3: as illustrated in FIG. 4, placing a displacement measurement equipment near the first measurement point 5 at a distance of 10-15 mm in the radial direction and piercing the mud layer 12 of the borehole wall and against the borehole wall, after the displacement measurement device 11 contacts the first measurement point 5, using a coring drill 13 to perform a radial cut around the displacement measurement device 9 to relieve the stress at the first measurement point 5, during the stress relief process, the displacement measurement device 11 continuously records the radial displacement change of the borehole wall during the stress relief process and transmits it to the ground in real time through a cable 14, after the displacement change is stable, the stress relief process is completed and the radial displacement value in one direction is obtained, wherein the size of the coring drill is between φ25-40 mm, and the stress relief depth is 40-65 mm, in this embodiment, the size of the coring drill is φ38.1 mm, and the stress relief depth is 63.5 mm;

S4: after the strain relief process is completed, cutting off the drilled core 15 by the coring drill 13, then rotating the sidewall coring device 3 and repeating the stress relief and sidewall coring operations at other measurement points to obtain radial displacement values in 6 different directions;

S5: after the measurement of all measurement points is completed, recovering the sidewall coring device 3 and removing the cores 15, and then measuring the elastic deformation parameters of each core, including the elastic modulus and Poisson's ratio through indoor supplementary tests, then combined with 6-9 radial displacement values in different directions obtained by high-precision displacement measurement, a set of linear equations including elastic deformation parameters, radial displacements and far-field stress are obtained, and the three-dimensional ground stress state of the measurement points is obtained.

Results show that the three-dimensional in-situ stress state at the deep part of shale gas exploration borehole measured by this method has high accuracy, and the measurement time of a single measurement point can be shortened to 15-20 minutes. At the same time, six cylindrical rock samples were obtained for further analysis and research, which is of great significance for the shale gas reservoir recoverability and resource reserve evaluation.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A method for determining three-dimensional in-situ stress based on displacement measurement of borehole wall, including the following steps:
S1: conducting well logging analysis in a shale gas exploration borehole or shale gas drilling borehole, and based on the results of the logging analysis, selecting a testing borehole section for in-situ stress testing, and then lowering a sidewall coring device to a depth of 2000-3000 meters, wherein the diameter of the shale gas exploration borehole is between 139.7 and φ339.725 mm;
S2: arranging 6-9 measurement points in the testing borehole section, and the measurement points are arranged on a closed curve, wherein the angles between a drilling axis of different measurement points is 55°-65°, and the distance in the axial direction is 90-120 mm;
S3: placing a displacement measurement equipment near a measurement point at a distance of 10-15 mm in the radial direction and piercing a mud layer of the borehole wall and against the borehole wall, after the displacement measurement device contacts the measurement point, using a coring drill to perform a radial cut around the displacement measurement device to relieve the stress at the measurement point, during the stress relief process, the displacement measurement device continuously records the radial displacement change of the borehole wall during the stress relief process and transmits it to a ground in real time through a cable, after the displacement change is stable, the stress relief process is completed and the radial displacement value in one direction is obtained, wherein the size of the coring drill is between 25-40 mm, and the stress relief depth is 40-65 mm;

S4: after the strain relief process is completed, cutting off the drilled core by the coring drill, then rotating the sidewall coring device and repeating the stress relief and sidewall coring operations at other measurement points to obtain radial displacement values in 6-9 different directions;

S5: after the measurement of all measurement points is completed, recovering the sidewall coring device and removing the cores, and then measuring the elastic deformation parameters of each core, including the elastic modulus and Poisson's ratio through indoor supplementary tests, then combined with 6-9 radial displacement values in different directions obtained by high-precision displacement measurement, a set of linear equations including elastic deformation parameters, radial displacements and far-field stress are obtained, and the three-dimensional ground stress state of the measurement points is obtained.

* * * * *